United States Patent [19]
Ren

[11] Patent Number: 5,843,042
[45] Date of Patent: Dec. 1, 1998

[54] ORAL MEDICINE DISPENSING DEVICE HAVING A METERED SYRINGE COMPONENT AND RESERVOIR

[76] Inventor: Liang Chen Ren, 44 Maple St., Bloomfield, N.J. 07003

[21] Appl. No.: 744,944

[22] Filed: Nov. 6, 1996

[51] Int. Cl.[6] ................................................ A61M 5/00
[52] U.S. Cl. .......................... 604/207; 604/77; 606/234
[58] Field of Search ............................ 604/77, 207, 208, 604/210, 211, 218; 606/234, 236

[56] References Cited

U.S. PATENT DOCUMENTS

| | | |
|---|---|---|
| 2,032,723 | 3/1936 | Schweser . |
| 3,212,685 | 10/1965 | Swan et al. . |
| 3,281,023 | 10/1966 | Bruck et al. . |
| 3,353,713 | 11/1967 | McLay . |
| 3,873,003 | 3/1975 | Jahn . |
| 4,189,065 | 2/1980 | Herold . |
| 4,269,331 | 5/1981 | Watson . |
| 4,560,352 | 12/1985 | Neümeister et al. . |
| 4,643,723 | 2/1987 | Smit . |
| 4,810,249 | 3/1989 | Haber et al. . |
| 5,017,190 | 5/1991 | Simon et al. ............................ 604/207 |
| 5,308,340 | 5/1994 | Harris ..................................... 604/208 |
| 5,328,486 | 7/1994 | Woodruff ............................... 604/208 |
| 5,454,793 | 10/1995 | Levander et al. . |
| 5,591,136 | 1/1997 | Gabriel .................................. 604/211 |

*Primary Examiner*—John D. Yasko

[57] ABSTRACT

A disposable or reusable oral medicine dispensing device, including a syringe housing having a lower fluid dispensing chamber for receiving medicinal fluid; a threaded plunger assembly mounted in the syringe housing for longitudinal movement relative to the syringe housing; a piston head rotatably mounted on the lower end of the threaded plunger assembly for longitudinal movement therewith; and a stop member threadedly mounted on the threaded plunger assembly to pre-set the distance between the stop member and the piston head to control the amount of medicinal fluid to be received in the lower fluid dispensing chamber of the syringe housing.

13 Claims, 11 Drawing Sheets

ORAL MEDICINE DISPENSING DEVICE HAVING A METERED SYRINGE COMPONENT AND RESERVOIR

FIELD OF THE INVENTION

The present invention relates to a disposable or re-usable oral medicine dispensing device for the precise metering and dispensing of a medicine to a patient orally. More particularly, it relates to a metered syringe component having an adjusting means to dispense a predetermined amount of medicine from a medicine reservoir to the patient.

BACKGROUND OF THE INVENTION

Syringes, metering dispensers, dispensing devices, and applicator devices for the dispensing of medicinal fluids have been overly intricate and because of their complexity, the non-medical operator does not have the skill nor the time for operating and maintaining these dispensing devices in good working condition for repeated use on a patient. Since these dispensing devices are primarily used for medicinal fluids, they must be routinely taken apart, cleaned and sterilized in order to prevent bacterial contamination and further illness to a patient, each time the medicine is given orally to a patient. Due to their complexity, there is a problem of constant disassembling, cleaning of the component parts, and then reassembling the dispensing device each time it is used.

There remains a need for an oral medicine dispensing device that will precisely dispense an exact quantity of a medicinal fluid repeatedly and in which there is a metered syringe component having an adjusting means that allows the repeated metering of the precisely defined quantity of medicinal fluid each time to the patient orally. In addition, the oral medicine dispensing device should be compact, self-contained, durable, re-usable, easy to clean and sterilizable for repeated administering of the patient's medicine.

DESCRIPTION OF THE PRIOR ART

Dispensers, syringes, and applicator devices for dispensing a fluid medium having various designs, structures, functions, and materials of construction have been disclosed in the prior art. For example, U.S. Pat. Nos. 3,212,685; 3,873,008; 4,189,065; 4,269,331; and 4,560,352 all disclose vernier-type dispensers, which are formed much like a syringe. The plunger component, however, does not slide in the barrel. Instead, the plunger is screwed inwardly to dispense fluid material from the barrel. In the '685 patent, instead of rotating the plunger, a nut mounted at the distal end of the barrel can be rotated to move the threaded plunger.

U.S. Pat. Nos. 3,281,023; 3,353,718; and 4,810,249 disclose a syringe that can be operated in either a conventional linear mode or in the vernier mode. These disclosed devices use slides, swinging latches or set screws to change the operational mode.

U.S. Pat. No. 4,643,723 shows a dispenser having a reservoir that can feed a separate pump chamber through a check valve. Another check valve allows the pump chamber to dispense through a needle. The travel of the piston rod is limited by a flange, but this travel is not adjustable. On the other hand, the downward motion of the piston rod can be set to one of two positions by turning an appendix member to one of the two positions within the dispenser. This prior art reference, however, does not have a threaded, adjustable stop as in the present invention.

U.S. Pat. No. 2,032,723 shows a syringe fitted with a three-way valve, so that the barrel can either be filled from a separate bottle during retraction of the piston, or dispensed through a needle during depression of the piston. The piston rod has a collar that can be screwed up and down along the length of the rod to act as an adjustable stop. In this embodiment, the stop is external and rotates. In contrast the stop member of the present invention is internal to the barrel and the piston rod rotates, where the stop member moves up and down. Also, this prior art reference does not disclose check valves to allow automatic refilling of the barrel.

U.S. Pat. No. 5,454,793 discloses a dispensing device having a threaded assembly that can be tilted to slide in and out of a slotted hollow housing. When placed in an aligned position, the threaded member can be screwed in and out to clamp onto a removable ampule. The ampule is dispensed by a conventional plunger. This device is unconcerned with metering a dose and does not have a reservoir separate from the ampule.

None of the prior art patents teach or disclose an internal stop member that can rotate up and down on a threaded plunger as the plunger is turned. In addition, none of the prior art patents teach or disclose a structure for a syringe type dispensing housing having a barrel component being integrally attached to a medicinal reservoir in which a check valve assembly is used for regulating the in-flow and out-flow of the medicinal fluid within the dispensing housing.

Accordingly, it is an object of the present invention to provide an oral medicine dispensing device which includes a metered syringe component having an adjusting means to allow for the metering and dispensing of a precisely defined quantity of a medicine to a patient.

Another object of the present invention is to provide an oral medicine dispensing device that includes a metered syringe component having a threaded plunger rotatably connected to a piston that is slidably mounted inside a hollow syringe barrel for receiving a precise quantity of medicine.

Another object of the present invention is to provide an oral medicine dispensing device that includes a syringe barrel having an integrally attached medicine reservoir compartment for supplying the patient's medicine to the metered syringe component.

Another object of the present invention is to provide an oral medicine dispensing device that includes a check valve assembly having an upper check valve member and a lower check valve gasket seal for regulating the flow of medicine from the medicine reservoir compartment into the fluid dispensing chamber of the metered syringe component.

Another object of the present invention is to provide an oral medicine dispensing device that includes a nipple attachment which can be hygienically sheathed with a disposable nipple cover such that it is removed after the medicine is administered to the patient.

A further object of the present invention is to provide an oral medicine dispensing device that is compact, self-contained, durable, disposable or re-usable, easy to clean, and sterilizable for repeated administering of the patient's medicine.

A further object of the present invention is to provide an oral medicine dispensing device that is easy to actuate and use by a non-professional to administer and dispense the medicine orally to a patient.

A still further object of the present invention is to provide an oral medicine dispensing device that can be mass produced in an automated and economical manner and is readily affordable by the user.

SUMMARY OF THE INVENTION

The present invention provides for an oral medicine dispensing device which includes a syringe housing having a lower fluid dispensing chamber for receiving medicinal fluid; a threaded plunger assembly mounted in the syringe housing for longitudinal movement relative to the syringe housing; a piston head rotatably mounted on the lower end of the threaded plunger assembly for longitudinal movement therewith; and a stop member threadedly mounted on the threaded plunger assembly to pre-set the distance between the stop member and the piston head to control the amount of medicinal fluid to be received in the lower fluid dispensing chamber of the syringe housing. In addition, the oral medicine dispensing device of the present invention further includes a medicine reservoir connected to the syringe housing and includes a fluid passageway for supplying medicinal fluid from the medicine reservoir to the lower fluid dispensing chamber of the syringe housing. Also, the oral medicine dispensing device of the present invention further includes a check valve assembly having an upper check valve member and a lower check valve gasket seal for regulating the medicinal fluid flow from the medicine reservoir to the syringe housing, and from the syringe housing to the discharge orifice section through which the medicinal fluid is orally received by a patient.

The oral medicine dispensing device of the present invention is formed of a heat resistant, clear material selected from the group consisting of a nylon composition, a plastic composition, a glass composition and combinations thereof, having a minimum heat resistant temperature of 220° F. in order to be sterilizable for repeated use.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein.

DETAILED DESCRIPTION OF THE PREFERRED AND ALTERNATE EMBODIMENTS

An oral medicine dispensing device in a preferred embodiment 10 and an alternate embodiment 400 of the present invention are represented in detail in FIGS. 1 through 16. The oral medicine dispensing devices 10 and 400 are used for providing and dispensing of a precise volumetric quantity of a medicinal fluid 12 orally to a human patient or animal by medical or non-medical personnel. In addition, dispensing devices 10 or 400 may be used for the precise dispensing of ingredients for food recipes or for the precise dispensing of liquid chemical additives (small quantities) for a liquid product (i.e. liquid detergents, ice melters) in a batch process operation. Dispensing devices 10 and 400 are made of a clear durable plastic, being heat resistant for sterilization procedures (above 220° F.), and re-usable for multiple oral usage or other applications.

In particular, oral medicine dispensing devices 10 and 400 are formed of a heat resistant, clear material selected from the group consisting of a nylon composition, a plastic composition, a glass composition and combinations thereof, having a minimum heat resistant temperature of 220° F. in order to sterilize for repeated use.

Preferred Embodiment 10

Figure 1:
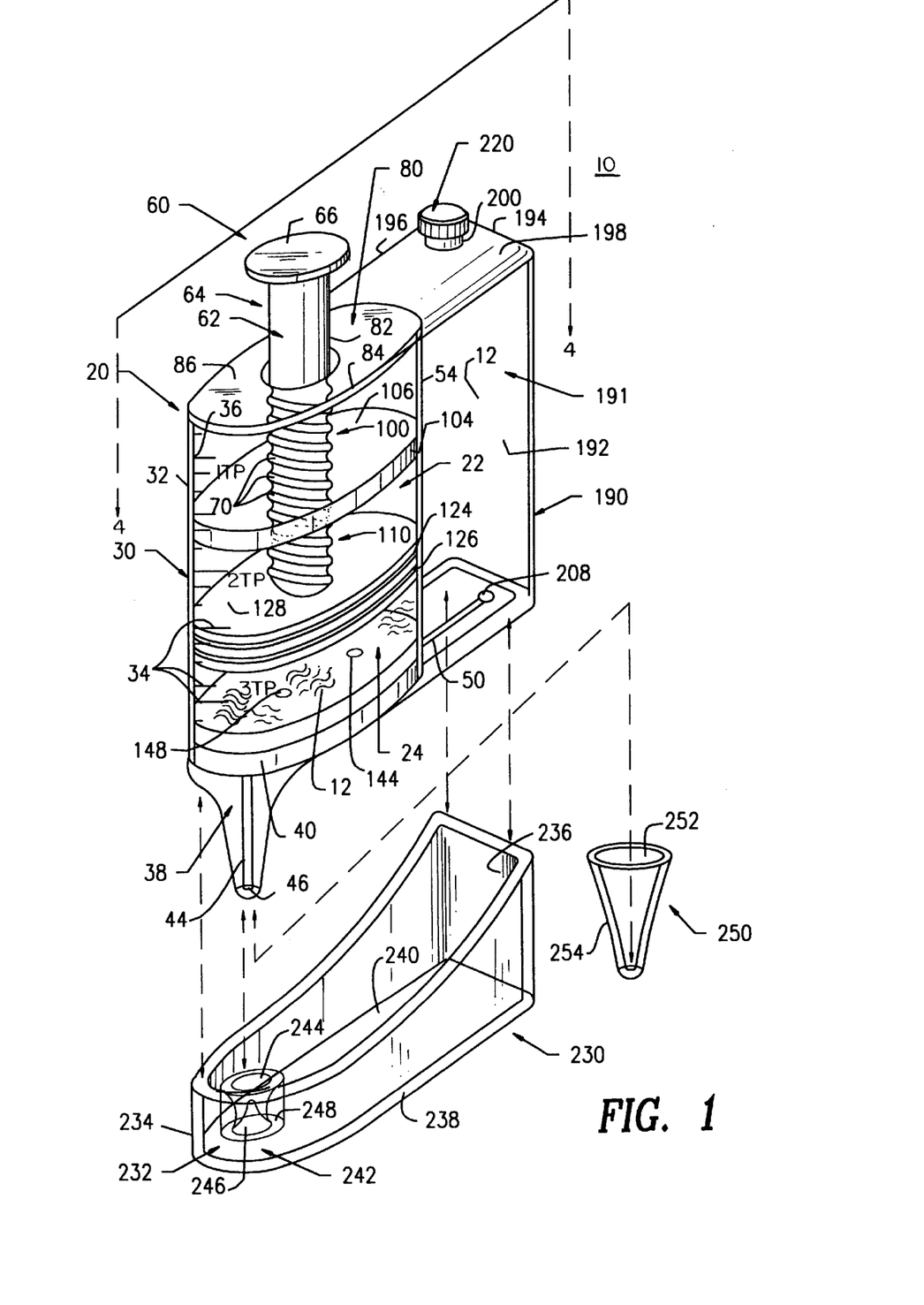
FIG. 1 is a partially exploded perspective view of the oral medicine dispensing device of the preferred embodiment of the present invention showing its component parts in an assembled state and in operational use.
Figure 2:
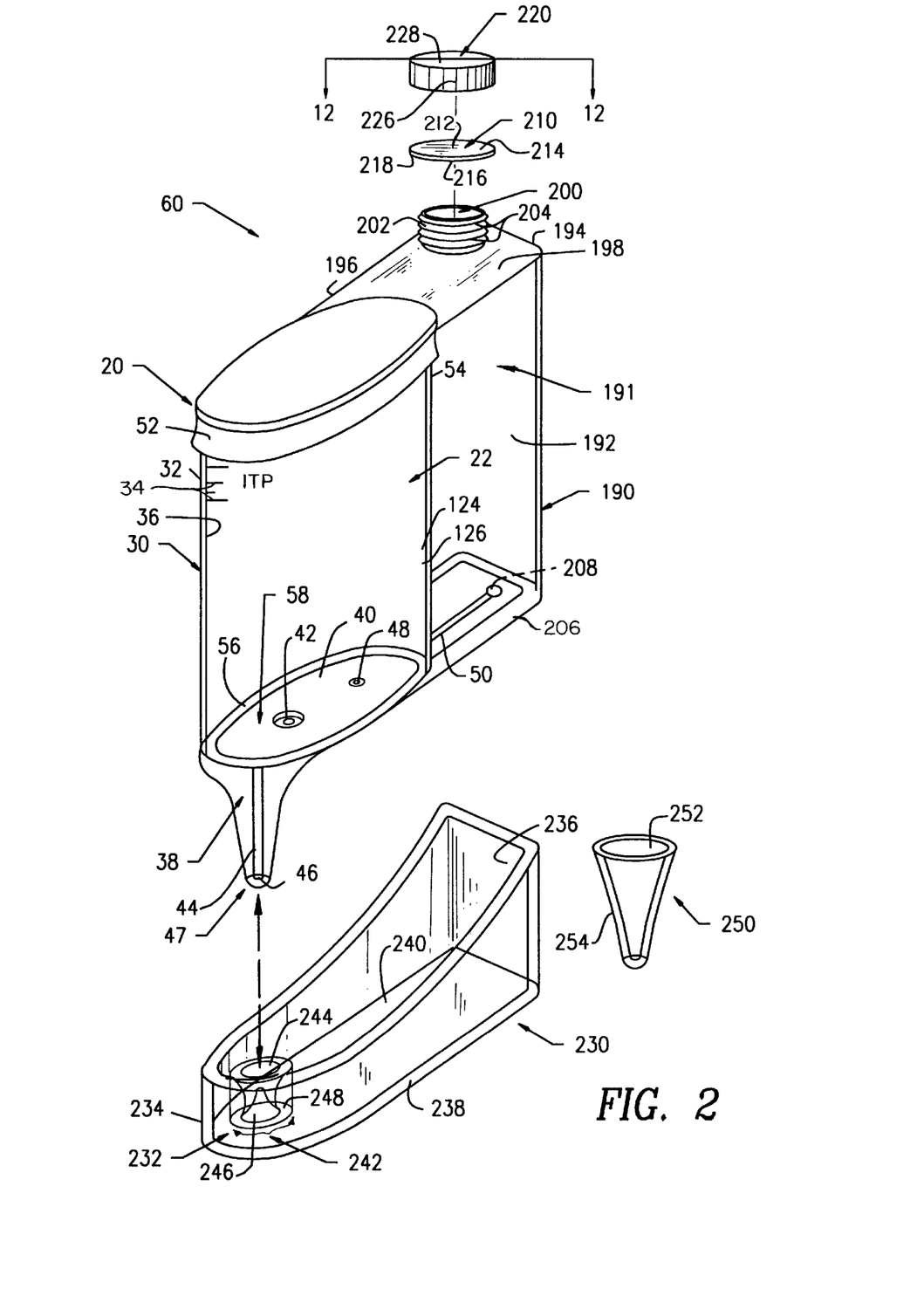
FIG. 2 is an exploded perspective view of the oral medicine dispensing device of the present invention showing the dispensing device housing having an integrally connected metered syringe component and a medicine reservoir compartment, a base stand, and a disposable orifice cover.
Figures 3A, 3B:
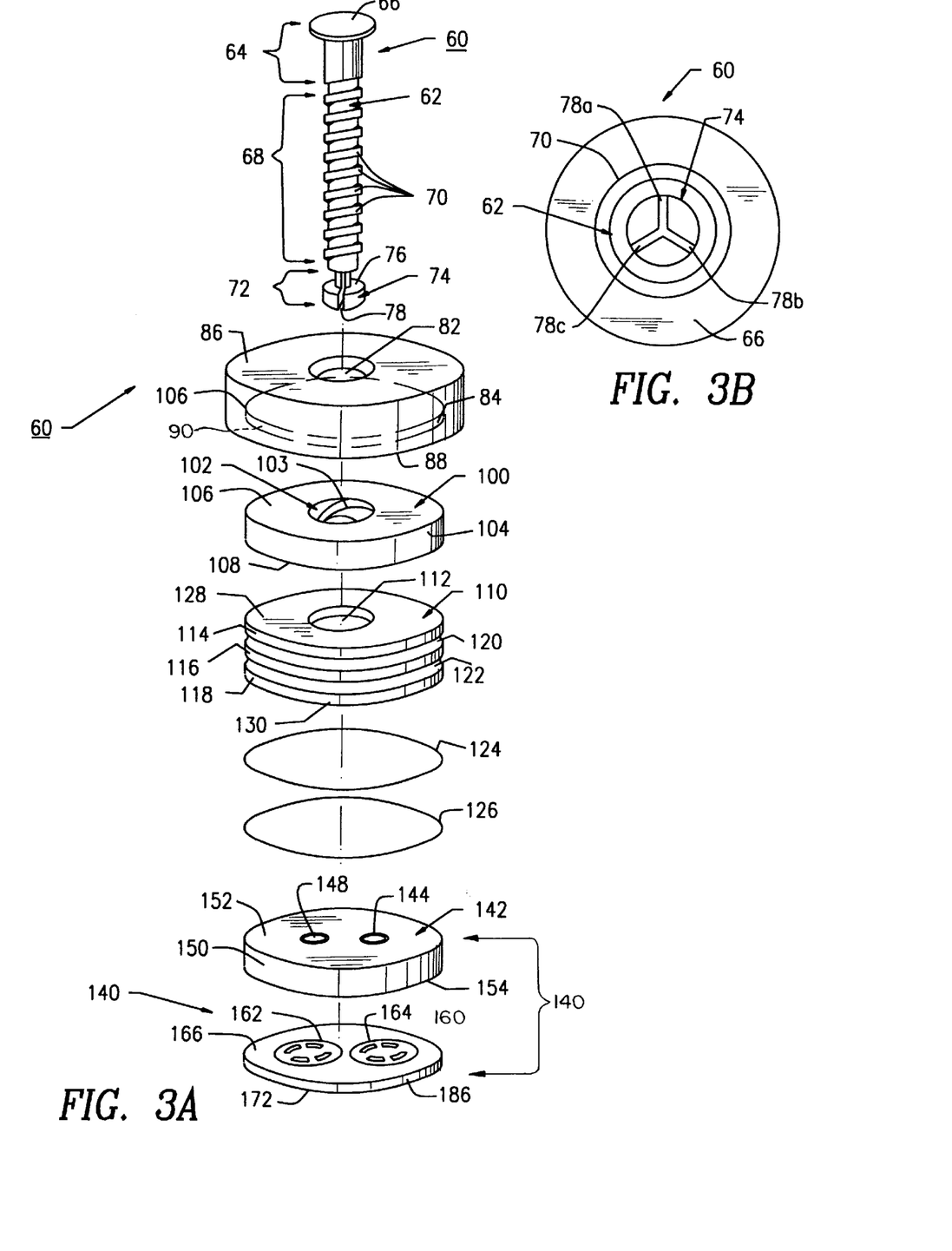
FIG. 3A is an exploded perspective view of the oral medicine dispensing device of the present invention showing the plunger component assembly and its component parts contained thereon.
FIG. 3B is an enlarged bottom plan view of the oral medicine dispensing device of the present invention showing the cylindrical shaft member and the piston tab member.
Figure 4:
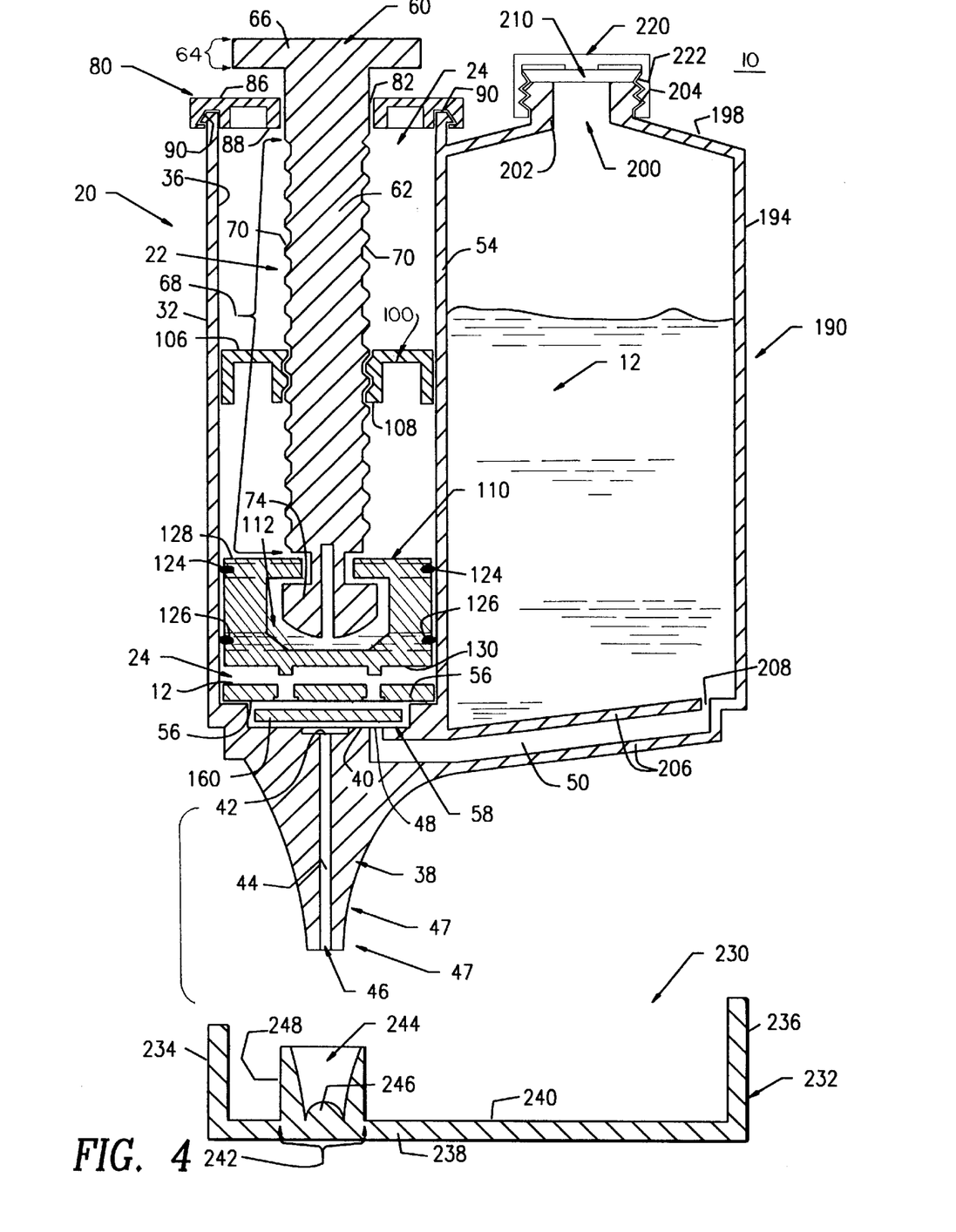
FIG. 4 is a vertical cross-sectional view of the oral medicine dispensing device of the present invention, taken along sectional line 4—4 of FIG. 1, showing the component parts contained therein, and in operational use.

The oral medicine dispensing device 10 of the preferred embodiment of the present invention is depicted in detail by FIGS. 1 through 12 of the drawings. Oral medicine dispensing device 10 includes a dispensing housing 20, as shown in FIGS. 1, 2, and 4, having an upper air chamber section 22 and a lower fluid chamber section 24 for holding of the medicinal fluid 12; a plunger component assembly 60; a check valve assembly 140; a base stand 230; and a disposable plastic cover 250 for covering the bottom discharge orifice section 38. The dispensing housing 20 further includes a metered, syringe-type barrel component 30 being oval-shaped having an integrally connected bottom discharge orifice section 38; and an integrally connected medicinal reservoir compartment 190 being substantially rectangular in shape. The medicinal reservoir 190 is used for holding of a medicinal fluid 12, and the barrel component 30 is integrally connected to the reservoir compartment 190 via the inner wall member 54.

The syringe-type barrel compartment 30 includes an outer side wall surface 32 having a plurality of striated markings 34 for indicating a finite volumetric quantity, in units such as milliliters (ml), cubic centimeters (cc), teaspoons (tsp), tablespoons (tbsp), and the like; an inner wall surface 36 being smooth; and an upper perimeter lip-edge 52 for receiving the snapon cover 80. The bottom discharge orifice section 38 includes a bottom wall 40 having a fluid outlet opening 42 for discharging the medicinal fluid 12 through a fluid passageway 44 to a discharge point 47 of an orifice/nipple outlet opening 46. In addition, fluid outlet opening 42 includes an annular recessed ring wall 43 having a plurality of nodes 45a, 45b, 45c, and 45d for providing a flow pathway for the medicinal fluid 12, as the medicinal fluid 12 passes through the fluid passageway or discharge fluid passageway 44 to the orifice outlet opening 46. Bottom wall 40 of discharge orifice section 38 further includes a fluid inlet opening 48 for receiving of medicinal fluid 12 via a second connecting fluid passageway or reservoir passageway 50; and an inner oval-shaped perimeter-edge wall 56 which forms a gasket seal compartment 58 for holding of lower gasket seal member 160. Second connecting fluid passageway 50 is connected to the medicinal reservoir compartment 190 via a circular fluid outlet opening 208.

The plunger component assembly 60, as shown in FIGS. 1, 3A, 3B and 4 includes a cylindrical shaft member 62, a snap-on cover 80, a stop plate member 100 and a piston head member 110. The plunger component assembly 60, as shown in FIGS. 3A, 3B, and 4, includes a cylindrical shaft member 62 having at the top end 64 a cap handle 66; at the center section 68 a helical threaded wall section 70; and at the lower end 72 a piston tab member 74 which detachably connects to the oval-shaped, piston head member 110. Piston tab member 74 includes a circular lip-edge perimeter wall 76 for interfitting within the piston tab receiving chamber 112 of piston head member 110, and three (3) vertical U-shaped channels 78a, 78b, and 78c which are used for compressing of the piston tab member 74 when it is received within the piston tab receiving chamber 112 of piston head member 110.

Plunger component assembly 60, as previously mentioned, incudes an oval-shaped snap-on cover 80, as shown in FIGS. 1, 3A, and 4, having a centrally located circular shaft opening 82 for receiving shaft member 62 therein, an outer oval-shaped side wall surface 84, a top wall 86, and a bottom wall 88. Bottom wall 88 includes an inner oval-shaped, and U-shaped channel opening 90 for receiving upper perimeter lip-edge 52 of barrel component 30, such that snap-on cover 80 interfits with the barrel component 30, as depicted in FIG. 4.

The stop plate member 100, as shown in FIGS. 1, 3A, and 4, is oval-shaped and includes a centrally located, circular opening 102 having an inner helical threaded wall 103; an outer oval-shaped side wall 104, a top wall 106 and a bottom wall 108. Stop plate member 100 is adjustably connected to the shaft member 62 for the purpose of providing a precise measured distance (volumetric quantity) between the piston head member 110 and the stop plate member 100. When the shaft member 62 is drawn upwardly within barrel component 30, then the top wall 106 of stop plate member 100 comes in contact with the bottom wall 88 of snap-on cover 80 and a precise volumetric quantity of medicinal fluid 12 is drawn-up into the lower chamber 24 from the medicinal reservoir compartment 190, such that the medicinal fluid 12 is contained between the piston head member 110 and the nipple/orifice opening 46 waiting to be orally discharged to the patient.

The oval shaped piston head member 110, as shown in FIGS. 1, 3A, and 4, includes a circular piston tab receiving chamber 112 for receiving of piston tab member 74 therein; outer oval-shaped side walls 114, 116, and 118 having two (2) U-shaped seal ring channels 120 and 122 set between the outer side walls 114 and 116; and 116 and 118, respectively, for receiving therein of two (2) seal rings 124 and 126 made of rubber, Teflon™ or plastic. The piston head member 110 further includes a top wall 128 and a bottom wall 130. Piston head member 110 is used for discharging of medicinal fluid 12 from the barrel component 30. This is done by the operator depressing the shaft member 62 downwardly, such that the bottom wall 130 of piston head member 110 is in contact with medicinal fluid 12 and the bottom wall 130 pushes the medicinal fluid 12 out of the lower fluid chamber 24 through nipple opening 46 and into the patient's mouth.

The check valve component assembly 140, as shown in FIGS. 1, 3A, and 4 to 9, includes an upper check valve member 142 and a lower check valve gasket seal 160. The check valve component assembly 140 is used for regulating of medicinal fluid 12 from the medicinal reservoir compartment 190 through the barrel component 30 and through the bottom discharge orifice section 38. As shown in FIG. 4, the check valve gasket seal 160 seats within the gasket seal compartment 58 of bottom wall 40, and the check valve member 142 is directly above lower check valve gasket seal 160, and in contact with it.

Figure 8:
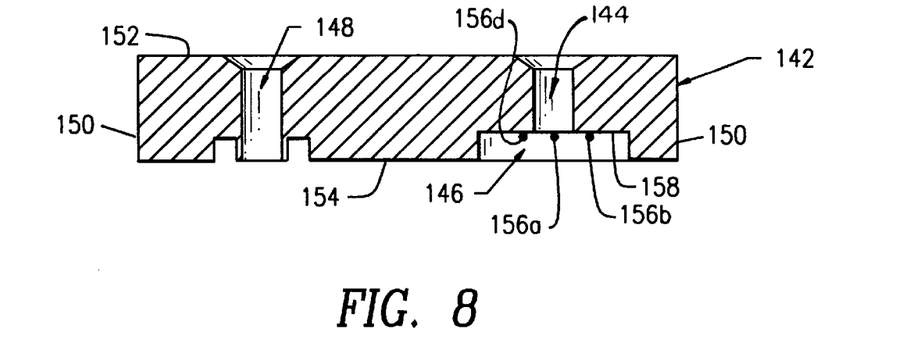
FIG. 8 is a cross-sectional view of the oral medicine dispensing device of the present invention, taken along sectional line 8—8 of FIG. 7, showing the upper check valve having a first fluid opening with a plurality of nodes for providing a medicine pathway, and a second fluid outlet opening.
Figure 9:
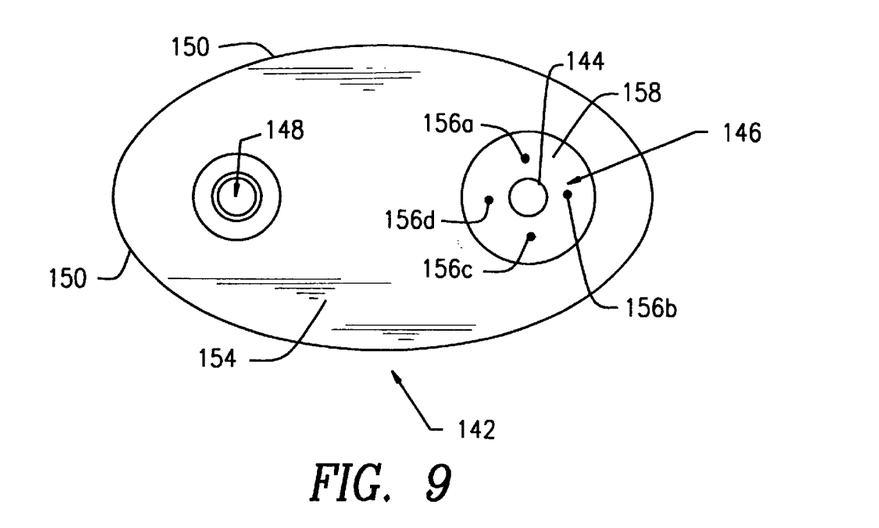
FIG. 9 is a bottom plan view of the oral medicine dispensing device of the present invention showing the upper check valve having a first fluid opening with a plurality of nodes for providing a medicine pathway, and a second fluid opening.
Figure 10:
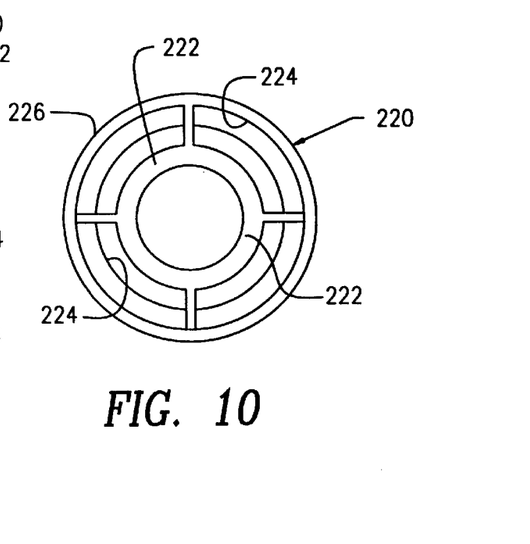
FIG. 10 is a bottom plan view of the oral medicine dispensing device of the present invention showing the reservoir cap having an inner air passageway for equalizing the air pressure within the medicinal reservoir compartment.

The upper check valve member 142, as shown in detail by FIGS. 5 to 9, includes two (2) equally-distant and centrally located fluid openings 144 and 148, an outer oval-shaped side wall 150, a top wall 152, and a bottom wall 154. The first fluid inlet opening 144 has a "T" shaped configuration 146 having a plurality of nodes 156a, 156b, 156c, and 156d located on the annular recessed inlet ring wall 158 of fluid opening 144. Nodes 156a to 156d, as depicted in FIGS. 8 and 9 of the drawings, are used for providing a pathway for the medicinal fluid 12 at either low or high pressures as it passes through the fluid inlet opening 144 to the lower fluid chamber 24 of barrel component 30.

Figure 5:
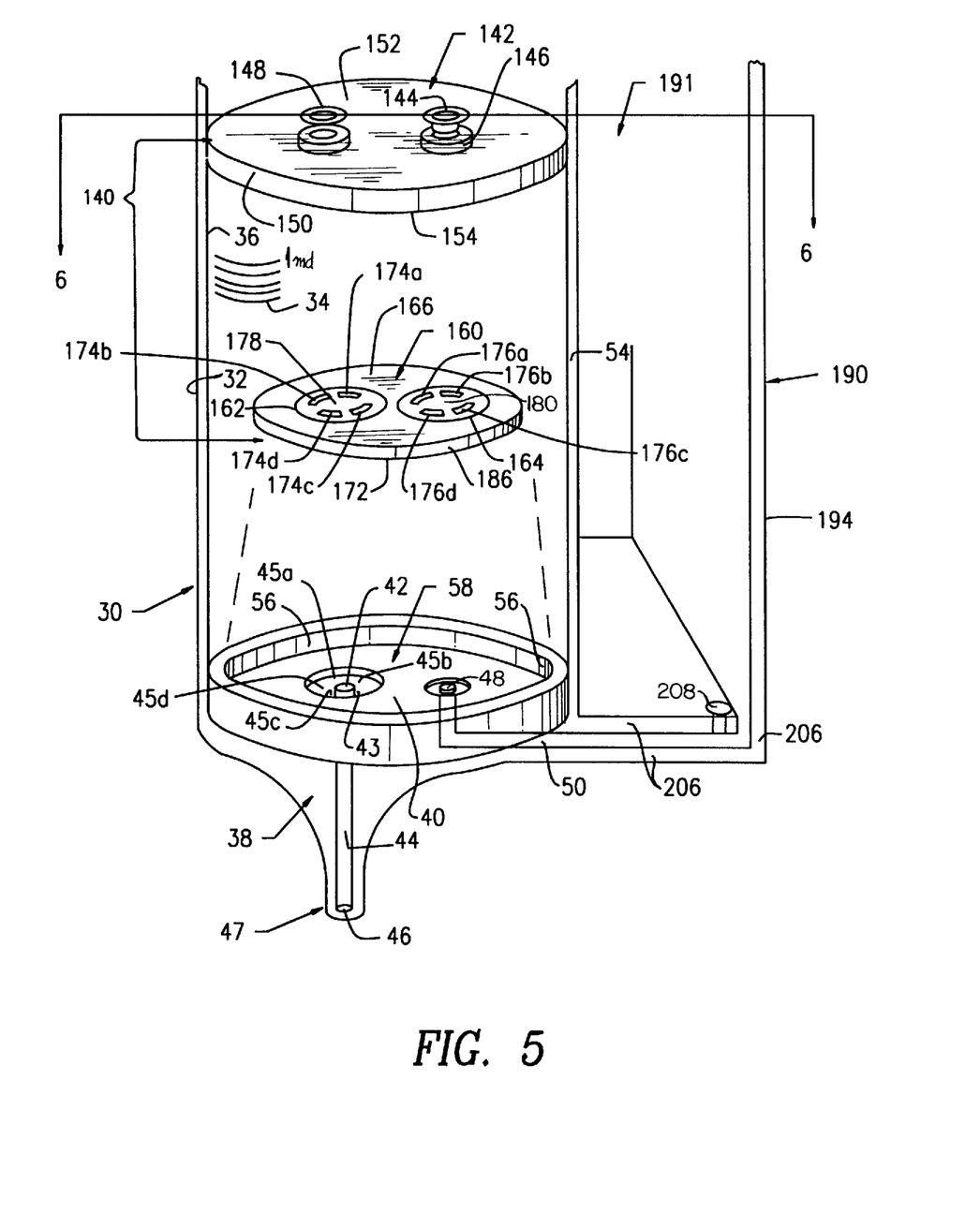
FIG. 5 is a partially exploded perspective view of the present invention showing the check valve assembly, the bottom discharge orifice section, and the lower portion of the medicine reservoir compartment.
Figure 6:
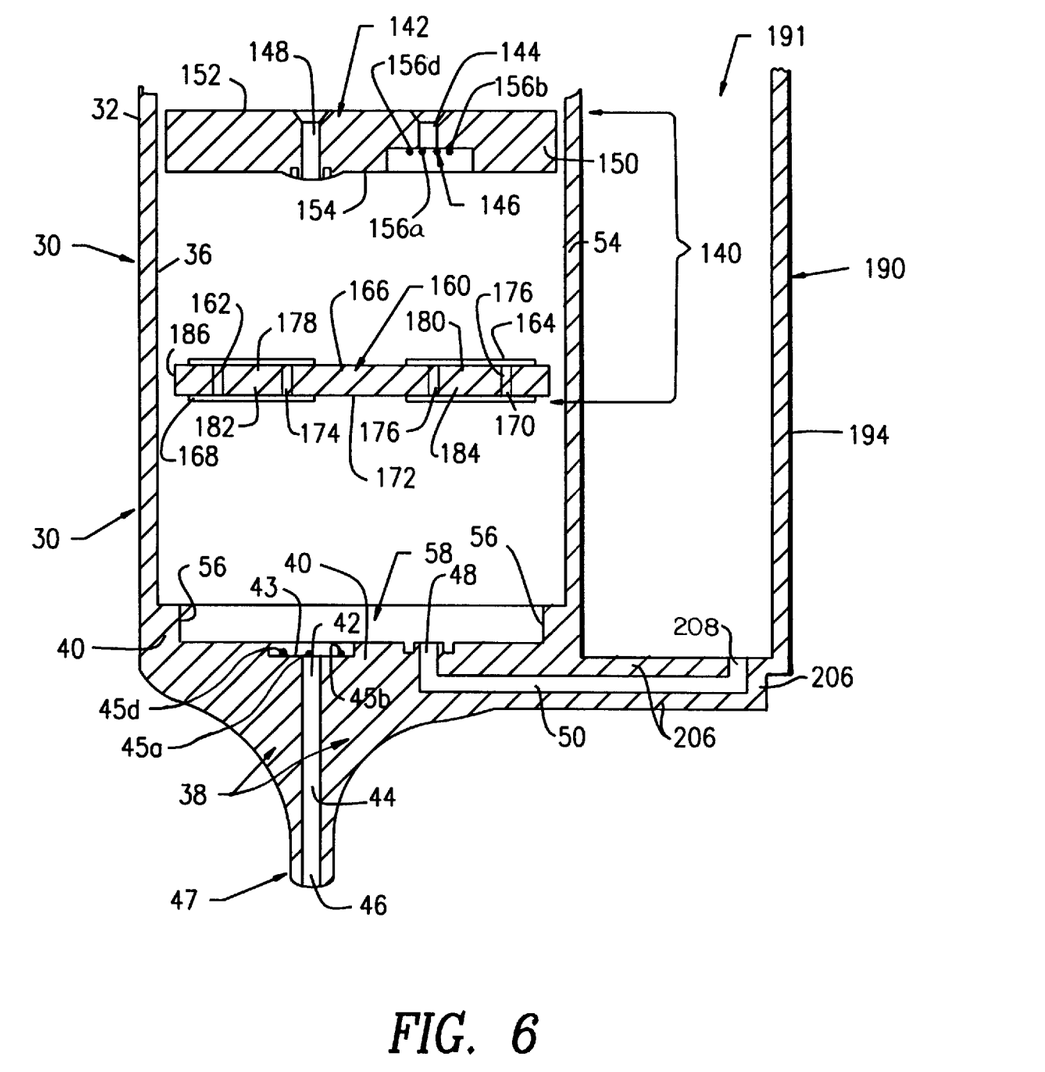
FIG. 6 is a partial vertical cross-sectional view of the oral medicine dispensing device of the present invention, taken along sectional line 6—6 of FIG. 5, showing the check valve assembly, the bottom discharge orifice section, and the lower portion of the medicine reservoir compartment.
Figure 7:
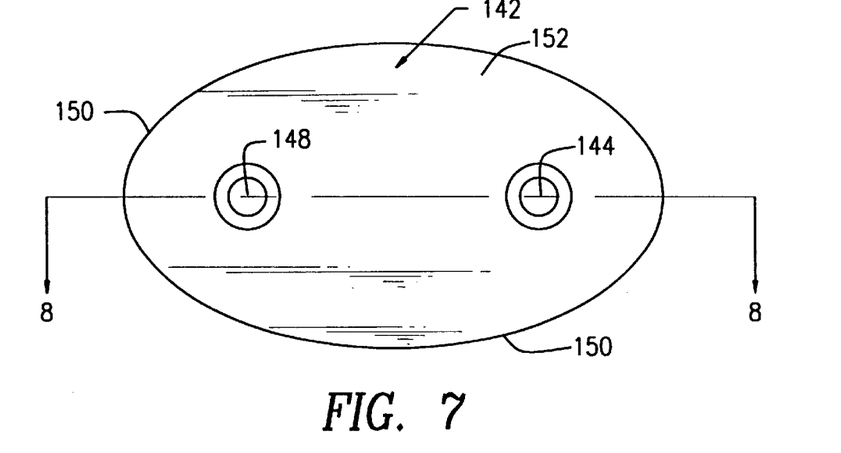
FIG. 7 is a top plan view of the oral medicine dispensing device of the present invention showing the upper check valve having a first fluid inlet opening and a second fluid outlet opening.

The lower check valve gasket seal 160, as shown in detail by FIGS. 5 and 6, includes two (2) sets of equally-distant and centrally located upper and lower circular seal rings 162, 164, 168, and 170, respectively, such that the upper seal rings 162 and 164 are integrally connected to the top wall surface 166 and the lower seal rings 168 and 170 are integrally connected to the bottom wall surface 172. Within each set of upper and lower circular seal rings 162 and 168; and 164 and 170, respectively, there are circular sectionalized fluid slot openings 174 and 176 through which medicinal fluid 12 passes. Upper and lower seal rings 162 and 168 include the circular sectionalized fluid slot openings 174a, 174b, 174c, and 174d. Upper and lower seal rings 164 and 170 include the circular sectionalized fluid slot openings 176a, 176b, 176c, and 176d. Check valve gasket seal 160 further includes upper circular seal areas 178 and 180, lower circular seal areas 182 and 184, and an outer oval-shaped side wall 186.

The upper circular seal areas 180 and 178 act as movable (tongue-like blockings seals) seals which operate to block or open the first fluid opening 144 and/or the second fluid opening 148, respectively, of upper check valve member 142. The lower circular seal areas 182 and 184 act as movable seals which operate to block or open the first fluid outlet opening 42 and/or the second fluid inlet opening 48, respectively, of bottom wall 40 of discharge orifice section 38. The regulating aspect of the flow of medicinal fluid 12 through the check valve component assembly 140 is further explained below in the operational use section.

The medicinal reservoir compartment 190 for holding a fluid medicine 12 is depicted in detail by FIGS. 1, 2, 4, 5, 6, 11, and 12 of the drawings. The medicinal reservoir compartment 190 is integrally connected to the syringe-type barrel component 30 by the inner wall member 54. Reservoir compartment 190 includes outer front, side, and rear walls 192, 194, and 196, a top wall 198 having a bottle neck opening 200 within a bottle neck 202, and a bottom wall 206 having a circular outlet opening 208 being connected to the second fluid passageway 50. Bottle neck 202 includes helical threaded wall edges 204 for receiving of reservoir cap 220.

Figure 11:
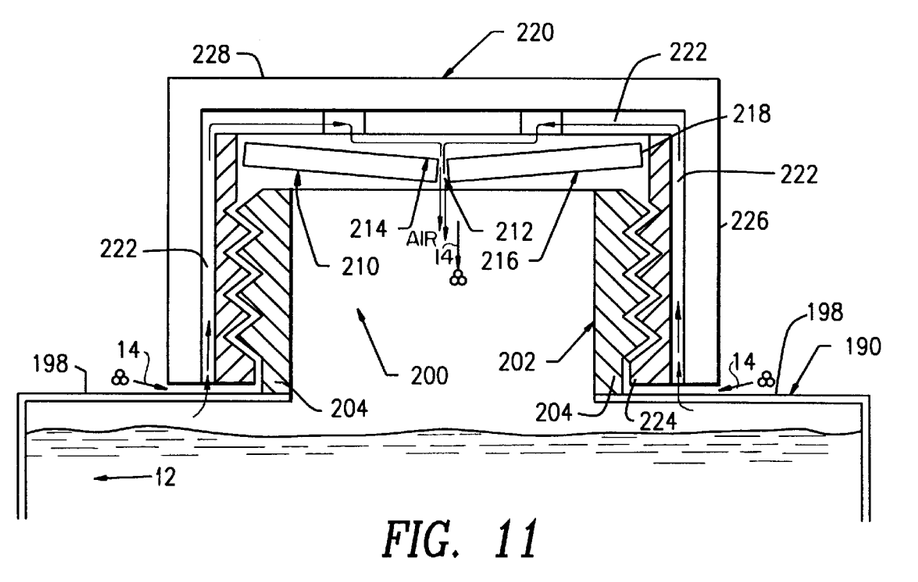
FIG. 11 is a cross-sectional view of the oral medicine dispensing device of the present invention showing the reservoir cap, and the rubber air seal plate gasket connected to the bottle neck of the medicinal reservoir compartment, and in an operational mode for supplying air to the reservoir compartment.
Figure 12:
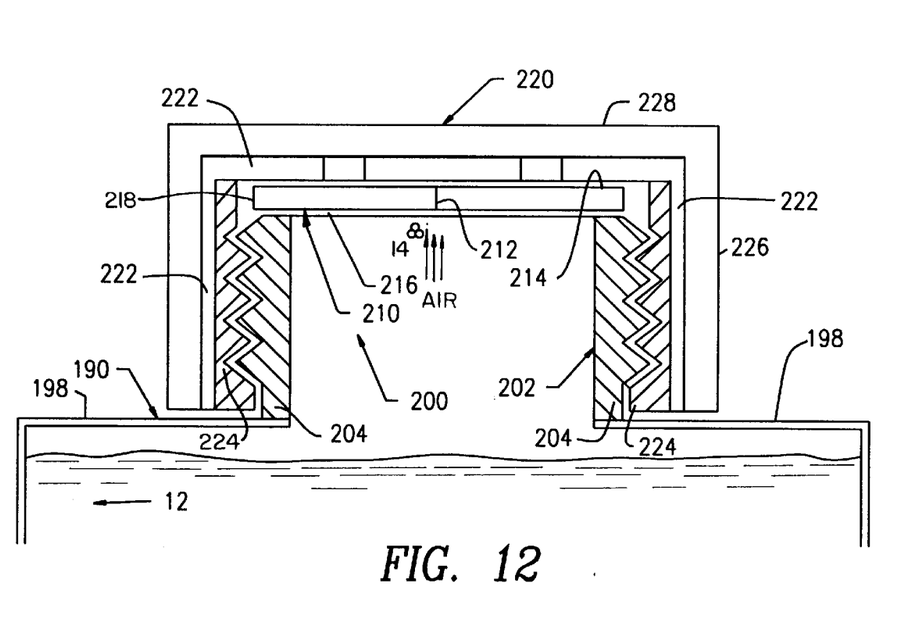
FIG. 12 is a cross-sectional view of the oral medicine dispensing device of the present invention showing the reservoir cap and the air seal plate gasket connected to the bottle neck of the medicinal reservoir compartment, and in an operational mode for stopping air from leaving the reservoir compartment.

Medicinal reservoir compartment 190 further includes a one-way air seal rubber plate gasket 210 which seats itself on the bottle neck opening 200 of bottle neck 202, as shown in FIGS. 11 and 12 of the drawings. The air seal gasket 210 provides a pressure mechanism in which to equalize the pressure within the reservoir compartment 190 to that of the outside air pressure. Air seal gasket 210 includes an air slit opening 212 for air 14, a top wall 214, a bottom wall 216, and a outer cylindrical wall surface 218.

The reservoir cap 220, as shown in detail in FIGS. 12 to 15, includes an inner air passageway 222 for the passing through of outside air 14, an inner threaded side wall 224 for receiving of the threaded wall edges 204 of bottle neck 202, an outer cylindrical grooved side wall 226 for gripping and a top wall 228.

The dispensing device base stand 230, as shown in FIGS. 1 and 2, includes a base stand housing 232 having an outer oval-shaped side wall 234, a rear wall 236, and a bottom wall 238 with an inner bottom wall surface 240. Bottom wall surface 240 includes at one end 242 an integrally attached nipple/orifice receiving compartment 244 for discharge orifice section 38. The nipple/orifice receiving compartment 244 includes a conical tab section 246 for receiving the nipple opening 46 of discharge orifice section 38 and outer cylindrical side wall 248, as shown in FIGS. 1 and 2.

In addition, the discharge orifice section 38 may include a cone-like disposable cover 250 which protects and covers discharge orifice section 38 of the oral medicine dispensing device 10 between operational uses of dispensing medicinal fluid 12 to a patient. Disposable cover 250 includes an inner conical wall 252 and an outer conical wall 254, as depicted in FIGS. 1 and 2 of the drawings.

Alternate Embodiment 400

The alternate embodiment of the oral medicine dispensing device 400 is depicted in FIGS. 13 through 16 of the drawings. Oral medicine dispensing device 400 include a syringe-type housing 410, as shown in FIG. 20, having an upper air chamber section 412 and a lower fluid chamber section 414; and a plunger component assembly 440. Syringe-type housing 410 further includes a metered barrel component 420 and a bottom discharge orifice section 430 having a conical shape. The barrel component 420 includes an outer oval-shaped side wall surface 422 having a plurality of striated markings 424 for indicating a finite volumetric amount, in units such as milliliters, teaspoons, tablespoons and the like; an inner wall surface 426; and an upper perimeter lip-edge 428 for receiving the snap-on cover 470. The bottom discharge orifice section 430 includes conical outer and inner wall surfaces 432 and 434; and a fluid outlet opening 436 for discharging the medicinal fluid 12.

The plunger component assembly 440, as shown in FIGS. 13 to 16, includes a cylindrical shaft member 450, a snap-on cover 470, a stop plate member 490, and a piston head member 500. The cylindrical shaft member 450 includes a cap handle 452, a helical threaded wall section 454, and a piston tab member 456 which detachably connects to the piston head member 500. The piston tab member 456 includes a circular lip-edge perimeter wall 458 for interfitting within the piston tab receiving chamber 502 of piston head member 500, and three (3) vertical U-shaped channels 460a, 460b, and 460c which are used for compressing of the piston tab member 456 when it is received within the piston tab receiving chamber 502 of piston head member 500.

The snap-on cover 470 includes a centrally located circular shaft opening 472 for receiving shaft member 450 therein, an outer oval-shaped side wall surface 474, a top wall 476, and a bottom wall 478 having an inner oval-shaped, U-shaped channel opening 480 for receiving of the upper perimeter lip-edge 428 of barrel component 420.

A stop plate member 490 is oval shaped and includes a centrally located, circular opening 492 having an inner helical threaded wall 493; an outer oval-shaped side wall 494; a top wall 496 and a bottom wall 498. Stop plate member 490 functions in the same manner as stop plate member 100, which was previously discussed in the preferred embodiment section.

A piston head member 500 is conically shaped and includes a piston tab receiving chamber 502, outer oval-shaped side walls 504, 506, and 508 having two (2) U-shaped seal ring channels 510 and 512 set between the outer side walls 504 and 506; and 506 and 508, respectively, for receiving therein of two seal rings 514 and 516 made of rubber, Teflon™, or plastic. The piston head member 500 further includes a top wall 518 and a bottom conically-shaped tab section 520 for interfitting into the bottom discharge orifice section 430. Piston head member 500 functions in the same manner as the piston head member 110 of the preferred embodiment 10.

OPERATION OF THE PRESENT INVENTION

Preferred Embodiment 10

To set-up the oral medicine dispensing device 10 of the preferred embodiment, the operator depresses the plunger component assembly 60 downwardly to the bottom most position, such that the bottom wall 130 of piston head member 110 is in contact with the top wall 152 of upper check valve member 142 of check valve assembly 140. The operator then rotatably adjusts the stop plate member 100 downwardly or upwardly, by manually turning the cap handle 66 of shaft member 62 clockwise for moving stop plate member 100 upwardly or counter-clockwise for moving stop plate member 100 downwardly. The positioning of stop plate member 100 within barrel component 30 at a given striated marking 34 determines the precise quantity of medicinal fluid 12 the patient will be given by the operator. The operator then checks that the snap-on cover 80 is securely fastened on the upper perimeter outer lip-edge 52 of barrel component 30 and that the plunger component assembly 60 moves freely upwardly and downwardly in the barrel component 30. The operator again depresses the plunger component assembly 60 to the bottom most position, as previously described.

Figure 14:
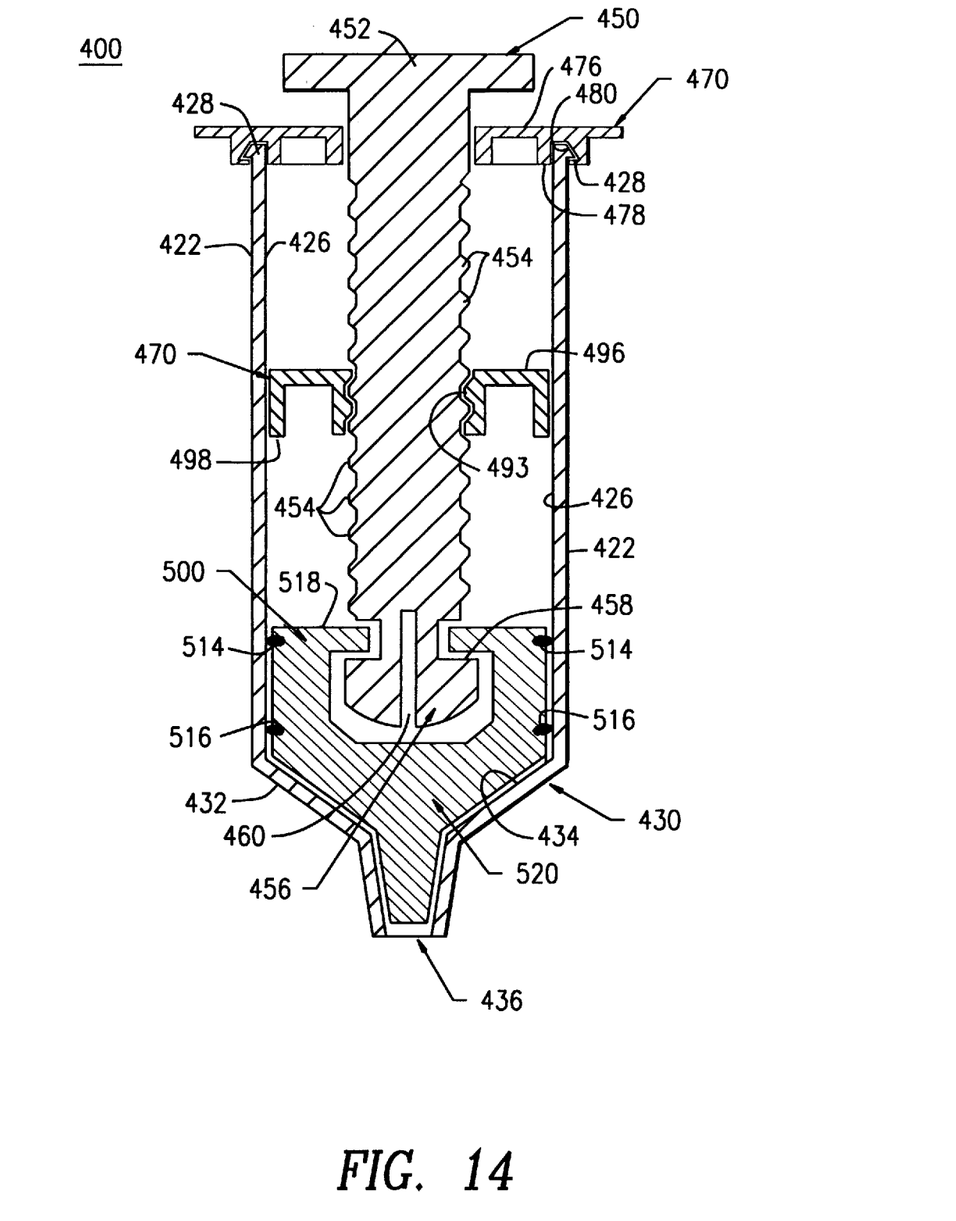
FIG. 14 is a vertical cross-sectional view of the oral medicine device for the present invention, taken along sectional line 14—14 of FIG. 13, showing the component parts contained therein, and in operational use.
Figure 15:
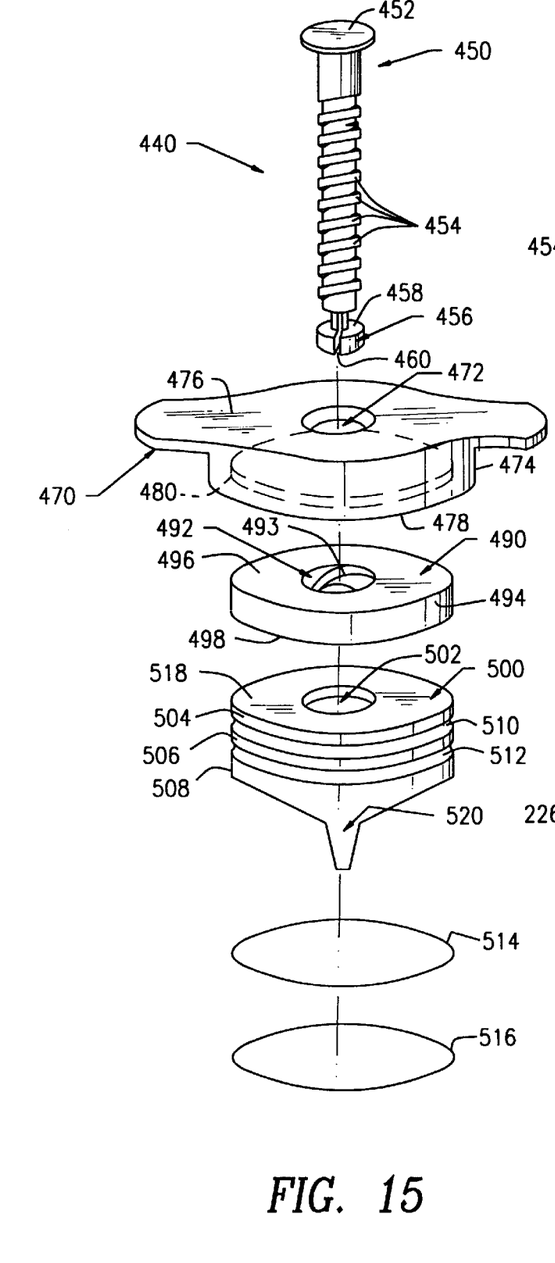
FIG. 15 is an exploded perspective view of the oral medicine dispensing device of the present invention showing the plunger component assembly and its component parts contained thereon.
Figure 16:
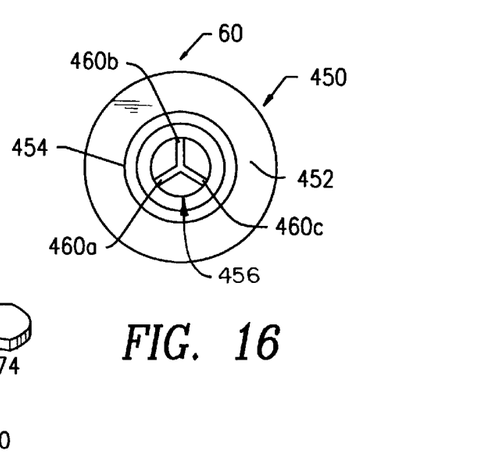
FIG. 16 is a bottom plan view of the oral medicine dispensing device of the present invention showing the cylindrical shaft member and the piston tab member.

Next, the operator removes the reservoir cap 220 and air seal plate gasket 210 from the bottle neck 202 of medicinal reservoir compartment 190. The operator then fills the reservoir compartment 190 via bottle neck opening 200 with a given medicinal fluid 12, as depicted in FIGS. 1, 14, and 15. The operator then places the air seal plate gasket 210 on the bottle neck opening 200 of bottle neck 202 and screws back the reservoir cap 220 on the bottle neck 202 tightly.

The oral medicine dispensing device 10 is now ready for operational use, such that the reservoir compartment 190 is full and the medicinal fluid 12 is ready to be transferred to the lower fluid chamber 24 of barrel syringe component 30. The operator now pulls the plunger component assembly 60 upwardly via cap handle 66. As the shaft member 62 moves the piston head member 110 upwardly, the pressure decreases below the check valve assembly 140. This action then draws the medicinal fluid 12 from the medicinal reservoir compartment 190 via fluid outlet opening 208 and second fluid passageway 50. The medicinal fluid 12 then travels through fluid reservoir passageway 50 to fluid inlet opening 48, such that the medicinal fluid 12 now goes through the sectionalized fluid slot openings 176a to 176d of lower check valve gasket seal 160. The lower seal area 184 pushes upwardly which opens the fluid opening 48 and medicinal fluid 12 pushes upwardly through the recessed annular ring section 146 of fluid opening 144. The plurality of nodes 156a to 156d, as shown in FIGS. 8 and 9, provide a pathway for the medicinal fluid 12 as it passes through the fluid inlet opening 144 to the lower fluid chamber 24 of barrel component 30 and is filled to the precise quantity as previously determined by the operator.

Concurrently, the upper seal area 178 of lower check valve gasket 160 pushes upwardly to close and seal-off the fluid outlet opening 148, such that the medicinal fluid 12 within lower fluid chamber 24 is held in place and is ready to be dispensed to the patient by the operator. Also, taking place at the same time, as shown in FIGS. 11 and 12, is the regulatory air pressure equalization process for the medicinal reservoir compartment 190. As shown in FIG. 11, the sequence for this process is that outside air 14 is taken in from the bottle neck 202 area of top wall 198. The air 14 passes through the inner air passageway 222 of reservoir cap 220, and the air 14 then passes through the air slit opening 212 of air seal gasket 210, and through bottle neck opening 200 to the inner reservoir compartment chamber 191 of the medicinal reservoir compartment 190. This aforementioned sequence equalizes the pressure in reservoir compartment chamber 191 of reservoir compartment 190 to that of the outside air pressure. Once the pressure has been equalized within reservoir chamber 191, as shown in FIG. 12 of the drawings, air 14 cannot pass through the air slit opening 212 of air seal gasket 210. The operator then places the protective cover 250 on the discharge nipple section 38.

The operator is now ready to dispense the medicinal fluid 12 to the patient by depressing the cap handle 66 of shaft member 62 downwardly, such that the piston head member 110 pushes the medicinal fluid 12 downwardly and out of the lower fluid chamber 24 of barrel component 30. Fluid 12 does not leak into the upper chamber 22 because of the seal rings 124 and 126 connected to the piston head member 110, as these seal rings 124 and 126 are always in contact with the inner wall surface 36 of barrel component 30. In this manner, they provide an air tight and liquid tight seal, as the piston head member 110 moves downwardly through the barrel component section 30, as shown in FIGS. 1 and 4. The medicinal fluid 12 then travels through fluid openings 148 and 174a to 174b of the check valve assembly 140 to fluid outlet opening 42. This sequence of flow occurs, as the lower seal area 182 is pushed downwardly (this action is caused by the downward pressure of medicinal fluid 12) which moves the medicinal fluid 12 through the recessed annular ring wall 43 of fluid outlet opening 42. The plurality of nodes 45a to 45d, as shown in FIGS. 5 and 6, provide a flow pathway for the medicinal fluid 12 as it passes through fluid outlet opening 42 and discharge fluid passageway 44 which then discharges the medicinal fluid 12 through the nipple discharge outlet opening 46 into the patient's mouth.

Concurrently, the lower seal area 184 of lower check valve gasket 160 pushes downwardly to close and seal-off the fluid inlet opening 48, such that there is no incoming flow of medicinal fluid 12 from the medicinal reservoir compartment 190 via the second fluid passageway 50.

After the operator has orally dispensed the medicinal fluid 12 from the dispensing device 10 to the patient, the operator can discard protective cover 250 and place the dispensing device 10 within the base stand 230. The nipple receiving compartment 244 of base stand 230 receives the discharge nipple section 38, such that the nipple outlet opening 46 is received on the cone tab 246 of compartment 244.

After the operator has completed the oral dispensing of the medicinal fluid 12 (several times) for a patient in a given day, the operator can discard or dismantle the dispensing device 10, and thoroughly clean, wash and rinse clean all of the component parts of dispensing device 10. The operator can then reassemble the dispensing device 10 with clean component parts. The operator then puts the clean dispensing device 10 in an autoclavable bag and sterilizes the dispensing device 10 appropriately. After sterilizing, the oral medicine dispensing device 10 is now ready to be used again for another or same medicinal fluid 12 for a given patient.

Alternate Embodiment 400

To set-up the oral medicine dispensing device 400 of the alternate embodiment, the operator depresses the plunger component assembly 440 downwardly to the bottom most position, such that the tab section conical wall 520 of piston head member 500 is in contact with inner conical wall surface 434 of the bottom discharge orifice section 430 of syringe housing 410. The operator then rotatably adjusts the stop plate member 490 downwardly or upwardly, by manually turning the cap handle 452 of shaft member 450 clockwise for moving stop plate member 490 upwardly or counterclockwise for moving stop plate member 490 downwardly. The positioning of stop plate member 490 within barrel component 420 at a given striated marking 424 determines the precise quantity of medicinal fluid 12 the patient will be given by the operator. The operator then checks that the snap-on cover 470 is securely fastened on the upper perimeter outer lip-edge 428 of barrel component 420 and that the plunger component assembly 440 moves freely upwardly and downwardly in the barrel component 420. The operator again depresses the plunger component assembly 440 to the bottom most position, as previously described above.

Next, the operator fills an open container (not shown) with the medicinal fluid 12 being used by the patient, and the operator then places the discharge orifice section 430 into the medicinal fluid 12 and draws the plunger component assembly 440 upwardly by the cap handle 452. As the operator proceeds to pull the plunger component assembly 440 upwardly through the lower fluid chamber section 414 of syringe barrel component 420, the medicinal fluid 12 is drawn in and fills the lower fluid chamber section 414 via fluid opening 436. The operator stops the drawing of the plunger component assembly 440 upwardly when the top wall 496 of the stop plate member 490 engages and contacts the bottom wall 478 of snap-on cover 470. The operator simultaneously checks to see if the medicinal fluid 12 has completely filled the lower fluid chamber section 414 with no air space under the conical tab section 520 of the piston head member 500.

Figure 13:
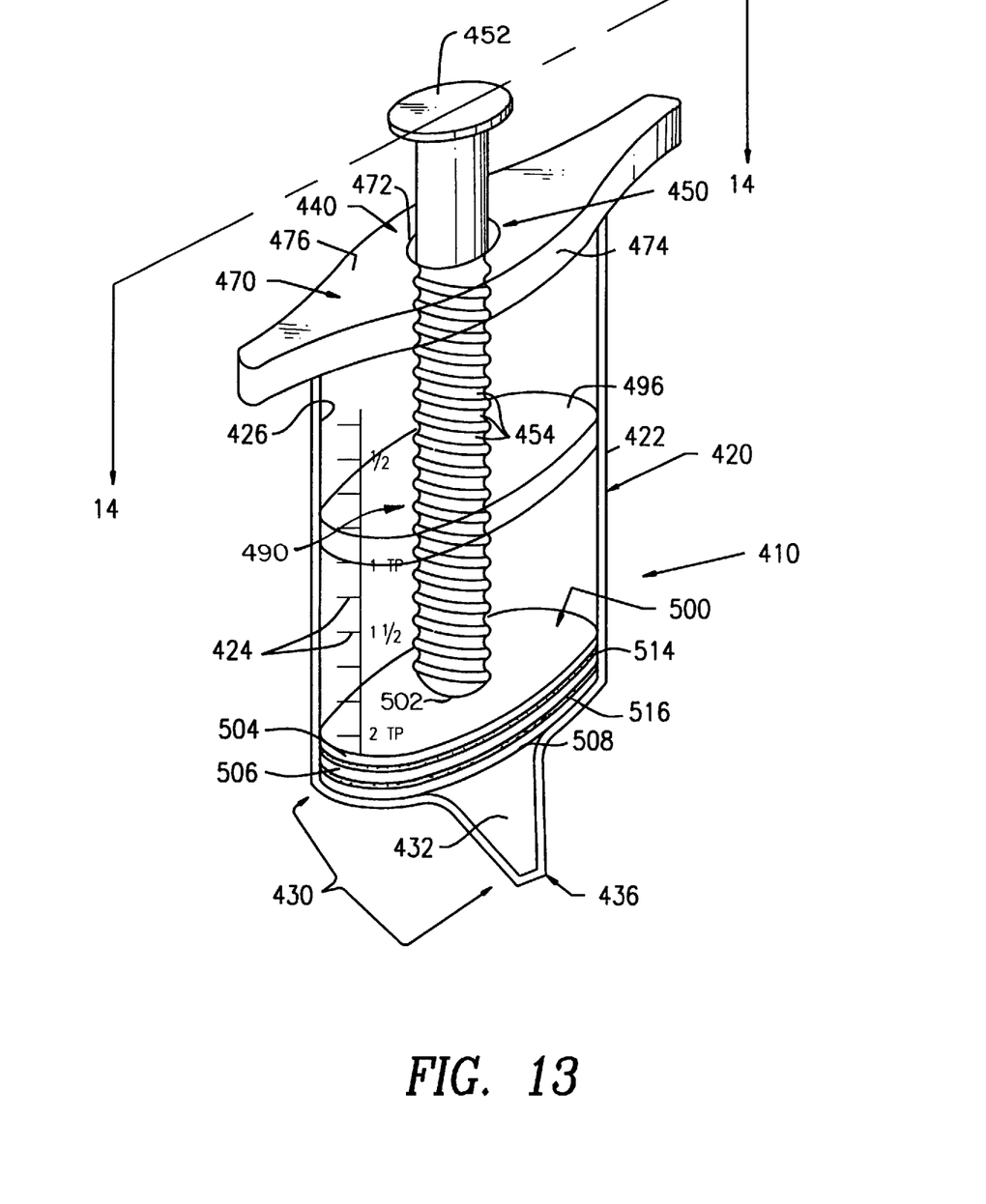
FIG. 13 is a perspective view of the oral medicine dispensing device of the alternate embodiment showing its component parts contained therein; and in an assembled state, ready for operational use.

The operator is now ready to dispense the medicinal fluid 12 to the patient by depressing the cap handle 452 of shaft member 450 downwardly, such that the piston head member 500 pushes the medicinal fluid 12 out of lower fluid chamber 414 of barrel component 420. Fluid 12 does not leak into the upper chamber 412 because of the seal rings 514 and 516 contained within U-shaped channels 510 and 512 of piston head member 500, as these seal rings 514 and 516 are in contact with the inner wall surface 426 of barrel component 420. In this manner, they provide air and liquid tight seals, as the piston head member 500 moves downwardly through the barrel component 420, as shown in FIGS. 13 and 14 of the drawings. The medicinal fluid 12 then travels through the bottom discharge orifice section 432 to the fluid outlet opening 436. The procedure is completed when the bottom conical tab section 520 of piston head member 500 interfits into the bottom discharge orifice section 430 and all of the medicinal fluid 12 has been discharged through fluid opening 436, as shown in FIGS. 13 and 14.

After the operator has completed the oral dispensing of the medicinal fluid 12 (several times) for a patient in a given day, the operator can discard or dismantle the dispensing device 400, and thoroughly clean, wash and rinse clean all of the component parts of dispensing device 400. The operator can then reassemble the dispensing device 400 with clean component parts. The operator then puts the clean dispensing device 400 in an autoclavable bag and sterilizes the dispensing device 400 appropriately. After sterilizing, the oral medicine dispensing device 400 is now ready to be used again for another or same medicinal fluid 12 for a given patient.

ADVANTAGES OF THE PRESENT INVENTION

Accordingly, an advantage of the present invention is that it provides for an oral medicine dispensing device which includes a metered syringe component having an adjusting means to allow for the metering and dispensing of a precisely defined quantity of a medicine to a patient.

Another advantage of the present invention is that it provides for an oral medicine dispensing device that includes a metered syringe component having a threaded plunger rotatably connected to a piston that is slidably mounted inside a hollow syringe barrel for receiving a precise quantity of medicine.

Another advantage of the present invention is that it provides for an oral medicine dispensing device that includes a syringe barrel having an integrally attached medicine reservoir compartment for supplying the patient's medicine to the metered syringe component.

Another advantage of the present invention is that it provides for an oral medicine dispensing device that includes a check valve assembly having an upper check valve member and a lower check valve gasket seal for regulating the flow of medicine from the medicine reservoir compartment into the fluid dispensing chamber of the metered syringe component.

Another advantage of the present invention is that it provides for an oral medicine dispensing device that includes a nipple attachment which can be hygienically sheathed with a disposable nipple cover such that it is removed after the medicine is administered to the patient.

A further advantage of the present invention is that it provides for an oral medicine dispensing device that is compact, self-contained, durable, disposable or re-usable, easy to clean, and sterilizable for repeated administering of the patient's medicine.

A further advantage of the present invention is that it provides for an oral medicine dispensing device that is easy to actuate and use by a non-professional to administer and dispense the medicine orally to a patient.

A still further advantage of the present invention is that it provides for an oral medicine dispensing device that can be mass produced in an automated and economical manner and is readily affordable by the user.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. An oral medicine dispensing device, comprising:

a) a syringe housing having a lower fluid chamber for receiving medicinal fluid to be dispensed; said lower fluid chamber being in one piece and integral with said syringe housing;

b) a threaded plunger assembly mounted in said syringe housing for longitudinal movement relative to said syringe housing;

c) a piston head rotatably mounted on the lower end of said threaded plunger assembly for longitudinal movement therewith; and d) a stop member rotatably mounted on said threaded plunger assembly to pre-set the distance between said stop member and said piston head to measure the amount of medicinal fluid to be received in the lower fluid chamber of said syringe housing.

2. An oral medicine dispensing device in accordance with claim 1, further including a medicine reservoir integral with said syringe housing and including a reservoir fluid passageway for supplying medicinal fluid from said medicine reservoir to said lower fluid chamber of said syringe housing.

3. An oral medicine dispensing device in accordance with claim 1, said plunger assembly further including a cover for covering said syringe housing and a threaded shaft member, said cover having a centrally located shaft opening for receiving said threaded shaft member.

4. An oral medicine dispensing device in accordance with claim 1, further including a discharge orifice section being integrally attached to said syringe housing and having a discharge passageway with a fluid outlet opening at one end and a nipple opening at the other end for discharging the medicinal fluid to a patient orally.

5. An oral medicine dispensing device in accordance with claim 4, wherein said fluid outlet opening of said discharge orifice section includes an annular recessed ring wall having a plurality of nodes thereon for providing a flow pathway for the medicinal fluid.

6. An oral medicine dispensing device in accordance with claim 2, further including a check valve assembly having an upper check valve member and a lower check valve gasket seal for regulating the medicinal fluid flow from said medicine reservoir to said syringe housing, and from said syringe housing to said discharge orifice section.

7. An oral medicine dispensing device in accordance with claim 6, wherein said upper check valve member includes a fluid inlet opening having an annular recessed ring wall with a plurality of nodes thereon for providing a flow pathway for the medicinal fluid, and a fluid outlet opening for discharging the medicinal fluid to a patient.

8. An oral medicine dispensing device in accordance with claim 6, further including a discharge orifice section having a fluid outlet opening, and wherein said lower check valve gasket seal includes two (2) sets of upper and lower circular seal rings; and within each of said two sets of upper and lower seal rings there are a plurality of circular sectionalized fluid slot openings for the passing through of medicinal fluid, and an upper and lower seal area which operate to block or open the fluid outlet opening of said discharge orifice section and said fluid inlet opening of said upper check valve member.

9. An oral medicine dispensing device in accordance with claim 1, wherein said medicinal reservoir includes an air seal gasket and a reservoir cap having air passageways for providing a pressure mechanism in which to equalize the pressure within said medicinal reservoir to that of the outside air pressure.

10. An oral medicine dispensing device in accordance with claim 1, wherein said dispensing device is formed of a heat resistant, clear material selected from the group consisting of a nylon composition, a plastic composition, a glass composition and combinations thereof, having a minimum heat resistant temperature of 220° F. for sterilizing said dispensing device for repeated use.

11. An oral medicine dispensing device in accordance with claim 1, further including a base stand for holding said dispensing device before and after use by the operator.

12. An oral medicine dispensing device in accordance with claim 1, wherein said piston head includes at least one channel for holding a seal ring which provides an air and liquid tight seal within said syringe housing.

13. An oral medicine dispensing device in accordance with claim 3, wherein said threaded shaft member includes a piston tab member for detachably connecting said piston head to said threaded shaft member.

* * * * *